United States Patent [19]

Chang et al.

[11] Patent Number: 4,743,401

[45] Date of Patent: May 10, 1988

[54] CONVERSION OF AN ALLYLIC ETHER TO ITS CORRESPONDING ACETAL

[75] Inventors: Biau-Hung Chang, West Chester; Ronnie M. Hanes, Milford, both of Ohio

[73] Assignee: National Distillers and Chemical Corporation, New York, N.Y.

[21] Appl. No.: 914,905

[22] Filed: Oct. 3, 1986

[51] Int. Cl.$^4$ .................. C11C 3/02; C07C 41/54
[52] U.S. Cl. .................. 260/410.9 R; 568/600; 568/603; 568/594; 560/186
[58] Field of Search .................. 568/600, 603, 594; 260/410.9 R; 560/186

[56] References Cited

U.S. PATENT DOCUMENTS

| | | | |
|---|---|---|---|
| 4,204,643 | 6/1980 | Shin | 568/600 |
| 4,313,893 | 2/1982 | Pesa | 568/594 |

*Primary Examiner*—Howard T. Mars
*Attorney, Agent, or Firm*—K. D. Tremain

[57] ABSTRACT

A process for converting an allylic ether to its corresponding acetal is disclosed. In this process an allylic ether is contacted with an organic hydroxy compound and a catalytically effective amount of a cobalt compound to produce the corresponding acetal.

25 Claims, No Drawings

CONVERSION OF AN ALLYLIC ETHER TO ITS CORRESPONDING ACETAL

BACKGROUND OF THE DISCLOSURE

1. Field of the Invention

The present invention is directed to the conversion of an allylic ether to its corresponding acetal. More specifically, the present invention is directed to the conversion of the ether group of an allylic ether to the corresponding acetal group by contacting the ether with an organic hydroxy compound in the presence of a cobalt catalyst.

2. Background of the Prior Art

The conversion of an allylic ether to its corresponding acetal is of significant commercial potential. Such a step, for instance, can be utilized in a synthesis route to the formation of the commercially important compound azelaic acid from readily available butadiene. Other commercial applications have also been identified or proposed.

The only prior art disclosing a process for converting an allylic ether to its corresponding acetal is Yamahara et al., Japanese Patent Publication No. 53-37,325. The Yamahara et al yield of acetal formation is low. Furthermore, the catalyst utilized in the Yamahara et al. disclosure is a ruthenium compound, a noble metal which is not only expensive but the halides thereof are also highly corrosive necessitating processing utilizing expensive, highly corrosive resistant materials such as titanium.

The above remarks establish the need in the art for a new process for converting allylic ethers to their corresponding acetal in commercial yield and selectivity. Moreover, a process is desired which can employ relatively low priced non-corrosive catalysts.

SUMMARY OF THE INVENTION

A new process has now been discovered which permits conversion of an allylic ether to its corresponding acetal in commercially exploitable yield and selectivity. Moreover, this process permits utilization of cheap non-corrosive catalysts.

In accordance with the present invention a process for converting the ether group of an allylic ether to its corresponding acetal is provided. In this process an allylic ether is contacted with an organic hydroxy compound and a catalytically effective amount of a cobalt compound which results in the formation of the corresponding acetal.

DETAILED DESCRIPTION

The present invention relates to a method for converting the ether group of an allylic ether to the corresponding acetal. An allylic ether has the formula

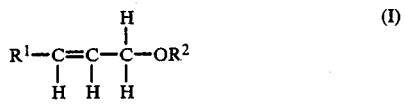

where $R^1$ is a cyclic or acyclic hydrocarbon group having from 1 to about 12, especially from 1 to about 10, carbon atoms $R^1$ preferably is an alkyl, alkenyl, aryl or alkaryl group or an alkyl, alkenyl, aryl or alkaryl group having ester, ether, acetal, formyl, ketone, carboxy or other functional groups. The radical $R^2$ also is a cyclic or acyclic hydrocarbon group having from 1 to about 12, especially from 1 to about 8, carbon atoms. Preferably, $R^2$ is an alkyl or aralkyl group. In the preferred embodiment wherein $R^1$ and $R^2$ are alkyl groups, structural isomers thereof are also intended to be included in the foregoing definition.

In a preferred embodiment the allylic ether of the present invention is provided with acetal or carboxylate functionality. That is, the allylic ether includes an acetal or carboxylate group. In Formula I, an allylic ether provided with acetal or carboxylate group is defined by the above definition of $R^1$ such that $R^1$ is a cyclic or acyclic hydrocarbon group having 1 to about 12, especially 1 to about 10, carbon atoms substituted with an acetal or carboxylate group, respectively.

A preferred class of allylic ethers, possessed of carboxylate functionality, that is reacted to form an acetal in accordance with the present invention are alkyl n-alkoxy-(n-2)-alkenoate compounds. These compounds are characterized by the limitation that n is an integer equal to the number of carbon atoms in the main chain of the alkenoate group. It is emphasized that the alkenoate main chain may be substituted with 1 or more alkyl groups. The alkoxy group is usually a lower alkoxy having from 1 to about 6 carbon atoms, preferably, from 1 to about 4 carbon atoms. The alkyl group also usually contains 1 to about 6 carbon atoms, preferably, 1 to about 4 carbon atoms. Finally, the alkenoate group usually contains 3 to about 12 carbon atoms, preferably, 3 to about 10 carbon atoms.

A particularly preferred class of alkenoates within the class of alkyl n-alkoxy-(n-2)-alkenoates of the present invention is the class of compounds where the alkenoate main chain contains 9 carbon atoms, i.e., n is 9. Such is the case where the alkyl n-alkoxy-(n-2)-alkenoate is alkyl 9-alkoxy-7-nonenoate. Among the nonenoates within this preferred class are methyl 9-methoxy-7-nonenoate, ethyl 9-ethoxy-7-nonenoate, methyl 9-ethoxy-7-nonenoate, methyl 9-propoxy-7-nonenoate, methyl 9-butoxy-7-nonenoate, ethyl 9-methoxy-7-nonenoate, ethyl 9-propoxy-7-nonenoate, propyl 9-methoxy-7-nonenoate, propyl 9-ethoxy-7-nonenoate and the like.

Another preferred class of allylic ethers that are converted to their corresponding acetals are those allylic ethers having acetal functionality and generically defined as 1,1,n-trialkoxy-(n-2)-alkene compounds. This preferred class of allylic ethers is characterized by an alkoxy usually having 1 to about 6 carbon atoms, preferably, 1 to about 4 carbon atoms and an alkene group usually having 3 to about 12 carbon atoms, preferably, 3 to about 10 carbon atoms. The alkene group can be substituted with one or more alkyl groups. The meaning of n in this preferred class of allylic ethers is an integer equal to the number of carbon atoms in the main chain of the alkene group.

A particularly preferred class of 1,1,n-trialkoxy-(n-2)-alkenes is the case where the alkene chain contains 9 carbon atoms, i.e., where n is 9. Some examples of compounds within this broad class of 1,1,9-trialkoxy-7-nonenes are 1,1,9-trimethoxy-7-nonene, 1,1,9-triethoxy-7-nonene, 1,1,9-tripropoxy-7-nonene, 1,1,9-tributoxy-7-nonene and the like.

The organic hydroxy compound of the present invention comprises any saturated or unsaturated organic compound having at least one hydroxy group. It may be a straight chain, branched chain, cyclic or heterocyclic compound and usually has from 1 to about 10 carbon atoms. Preferably, the organic hydroxy compound is an alkanol having from 1 to about 10 carbon atoms. More preferably, the alkanol is a lower alkanol having from 1 to about 6 carbon atoms. Still more preferably, the alkanol contains 1 to about 4 carbon atoms. Most preferably, the alkanol is methanol.

Other hydroxy compounds that may be used in accordance with the present invention include glycols such as 1,2-ethylene glycol, 1,2-propylene glycol, 1,3-propanediol, 1,2-butanediol, 1,3-butanediol and the like. Additionally, various mixtures of any of the foregoing organic hydroxy compounds may also be employed according to one embodiment of the present invention.

The process of the present invention involves reacting one of the aforesaid ethers with an organic hydroxy compound of the type discussed above in the presence of a catalytically effective amount of a cobalt catalyst. The cobalt catalyst of the present invention is preferably a cobalt coordination compound or a cobalt salt.

In the preferred embodiment wherein a cobalt coordination compound is employed the compound is preferably dicobalt octacarbonyl or a cobalt carbonyl with a ligand. The ligand may be a phosphine, a phosphite or a nitrogen-containing compound. Among the nitrogen-containing compounds preferred for use as the ligand are aliphatic amines such as triethylamine and heterocyclic aromatics such as pyridine. Of these, pyridine is particularly preferred.

In the alternate preferred embodiment wherein a cobalt salt is utilized, cobalt alkanoates and cobalt halides are particularly preferred. Of the halides, the chloride is usually employed.

In a particularly preferred embodiment of the process of the present invention, carbon monoxide is utilized. Although carbon monoxide gas is not a reactant, its presence is important to the effectiveness of the cobalt catalyst in the catalytic reaction of this invention.

The reaction of the process of the present invention preferably occurs at a temperature in the range of between about 140° C. and about 250° C. and a pressure in the range of between about 300 and 4,000 psig. More preferably, process of the present invention occurs under anhydrous conditions at a temperature in the range of between about 150° C. and about 180° C. and a pressure in the range of between about 500 and about 1,000 psig. This pressure is provided in whole or in part by carbon monoxide. In a preferred embodiment it is desirable to include hydrogen gas in the reaction. Although the partial pressure of the hydrogen gas is relatively minor, compared to that of carbon monoxide, its presence improves the effectiveness of the process of this invention.

The following examples are given to illustrate the present invention. In that these examples are provided solely for illustrative purposes, the invention should not be limited thereto.

EXAMPLE 1

A 71 ml Parr [trademark] bomb was charged with 3 ml. 1,1,9-trimethoxy-7-nonene; 3 ml methanol and 0.1 g. cobalt chloride. The bomb was purged three times with carbon monoxide. Thereafter, the bomb was pressurized to 500 psig with carbon monoxide gas. A final pressure of 600 psig was obtained by further pressurization with hydrogen gas. The pressurized bomb was heated to 160° C. and held at these thermodynamic conditions for 6 hours.

The product of this reaction was analyzed by gas chromotographic means. This analysis indicated the presence of 0.25 ml of 1,1,9,9-tetramethoxynonane. This represented a yield of 8%.

EXAMPLE 2

A Parr [trademark] bomb was charged with the same ingredients and amounts as in Example 1. The bomb was then purged four times with hydrogen gas. The bomb was thereafter pressurized to 300 psig with hydrogen gas and heated to 160° C. The bomb was maintained at these conditions for 6 hours.

The product of this reaction was analyzed by gas chromotographic means. The product was found to include 0.2 mol. of 1,1,9,9-tetramethoxynonane representative of a yield of 7%.

EXAMPLE 3

A glass bottle was charged with 30 g. methyl 9-methoxy-7-nonenoate (MMNE); 5.3 g. pyridine; 19.2 g. methanol; and 3.5 g. pentamethylbenzene, a gas chromatography standard, and the contents mixed. It is noted that the methyl 9-methoxy-7-nonenoate was 71.5% pure. Thus, the MMNE contained 21.45 g. MMNE; 4.06 g. methyl 8-methoxy-2-methyl-6-octenoate (MMMO); 0.14 g. of the desired product, methyl 9,9-dimethoxynonanoate (MDNA); 0.62 g. methyl 8,8dimethoxy-2-methyloctanoate (MDMO); and 3.73 g. of the impurities derived from carbomethoxylation of 8-methoxy-1, 6-octadiene. The mixture was added to a nitrogen gas-purged 300 ml. autoclave reactor along with 1.02 g. cobalt carbonyl having the structural formula $Co_2(CO)_8$ which was separately charged from a vial.

The reactor was sealed, purged three times with carbon monoxide and pressurized to 40 psig with hydrogen gas. The total pressure was increased to 690 psig by the addition of 650 psig carbon monoxide gas. The reactor was heated to 170° C. and carbon monoxide gas added to bring the pressure up to 1,000 psig. The reactor was maintained at these conditions for 4 hours with samples taken hourly.

Each of the hourly samples was analyzed by gas chromatographic means. The results of this sampling is tabulated below in Table 1.

TABLE 1

| Time, hr. | OVERALL CONVERSION OF MMNE AND MMMO (%) | OVERALL SELECTIVITY TO MDNA AND MDMO (%) |
|---|---|---|
| 1 | 95.3 | 93.1 |
| 2 | 96.0 | 88.3 |
| 3 | 96.9 | 83.2 |
| 4 | 97.6 | 81.4 |

Footnotes
MDNA is methyl 9,9-dimethoxynonanoate
MDMO is methyl 8,8-dimethoxy-2-methyloctanoate
MMNE is methyl 9-methoxy-7-nonenoate
MMMO is methyl 8-methoxy-2-methyl-6-octenoate

EXAMPLE 4

The autoclave reactor of Example 3 was charged with the same components in the same amounts as in Example 3. The reactor was pressurized to 500 psig (480 psig CO and 20 psig $H_2$) and heated to 170° C. The reactor was maintained at these conditions for 3 hours with samples taken at 30 minutes, 1 hr., 2 hrs. and 3 hrs.

The results of this run is tabulated in Table 2.

TABLE 2*

| Time, hr. | OVERALL CONVERSION OF MMNE AND MMMO (%) | OVERALL SELECTIVITY TO MDNA AND MDMO (%) |
| --- | --- | --- |
| 0.5 | 90.2 | 95.9 |
| 1 | 93.9 | 93.9 |
| 2 | 94.6 | 91.9 |
| 3 | 95.4 | 90.2 |

*Same meanings as defined in footnotes of Table 1

EXAMPLE 5

Example 4 was repeated except that the temperature of reaction was changed to 150° C. and the time of reaction was increased to 4 hours. Samples were taken at 0.5 hr., 1 hr., 2 hrs., 3 hrs. and 4 hrs.

The results of this example are summarized below in Table 3.

TABLE 3

| Time, hr. | OVERALL CONVERSION OF MMNE AND MMMO (%) | OVERALL SELECTIVITY TO MDNA AND MDMO (%) |
| --- | --- | --- |
| 0.5 | 62.3 | 85.9 |
| 1 | 87.7 | 82.9 |
| 2 | 95.4 | 89.5 |
| 3 | 97.3 | 92.6 |
| 4 | 97.8 | 86.8 |

*Same meanings as footnotes of Table 1.

EXAMPLE 6

Example 4 was repeated except for the temperature of reaction which was maintained at 160° C.

The results of this example are tabulated in Table 4 below.

TABLE 4*

| Time, hr. | OVERALL CONVERSION OF MMNE AND MMMO (%) | OVERALL SELECTIVITY TO MDNA AND MDMO (%) |
| --- | --- | --- |
| 0.5 | 85.0 | 92.1 |
| 1 | 94.2 | 90.6 |
| 2 | 96.4 | 91.2 |
| 3 | 96.4 | 90.6 |

*Same meanings as footnotes of Table 1

EXAMPLE 7

Example 3 was repeated with only minor differences in purity of the starting methyl 9-methoxy-7-nonenoate (MMNE) which contained 24.10 g. MMNE; 2.04 g. MMMO; 0.21 g. MDNA; and 0.63 g. MDMO. The example differed from Example 3 also in that the cobalt catalyst included 0.026 g. $Co_2(CO)_8$ but no pyridine. This example was conducted for 3 hours. Samples were taken at 0.5 hr., 1 hr., 2 hrs., and 3 hrs.

The example is summarized below in Table 5.

TABLE 5*

| Time, hr. | OVERALL CONVERSION OF MMNE AND MMMO (%) | OVERALL SELECTIVITY TO MDNA AND MDMO (%) |
| --- | --- | --- |
| 0.5 | 95.4 | 97.4 |
| 1 | 97.2 | >99.0 |
| 2 | 97.4 | >99.0 |
| 3 | 98.3 | >99.0 |

*Same meanings as footnotes of Table 1.

EXAMPLE 8

Example 7 was repeated except for that it was run in the absence of hydrogen. The cobalt catalyst was 0.10 g. $Co_2(CO)_8$.

The results of this example are tabulated in Table 6 below.

TABLE 6*

| Time, hr. | OVERALL CONVERSION OF MMNE AND MMMO (%) | OVERALL SELECTIVITY TO MDNA AND MDMO (%) |
| --- | --- | --- |
| 0.5 | 21.8 | 95.9 |
| 1 | 41.6 | 89.4 |
| 2 | 67.7 | 91.1 |
| 3 | 81.9 | 93.1 |

*Same meanings as footnotes of Table 1.

The above preferred embodiments and examples are given to illustrate the scope and spirit of the present invention. These embodiments and examples will make apparent, to those skilled in the art, other embodiments and examples. These other embodiments and examples are within the contemplation of the present invention. Therefore, the present invention should be limited only by the appended claims.

What is claimed is:

1. A process for converting the ether group of an allylic ether to its corresponding acetal comprising contacting an allylic ether selected from the group consisting of an alkyl n-alkoxy-(n-2)-alkenoate and 1,1,n-trialkoxy-(n-2)-alkene, where n is an integer equal to the number of carbon atoms in the alkenoate or alkene main chain independent of any substitution thereon by one or more alkyl groups, an alkanol and a catalytically effective amount of a cobalt compound whereby an acetal selected from the group consisting of alkyl n,n-dialkoxyalkanoate and 1,1,n,n-tetra-alkoxyalkane, respectively, where n has the meanings given above, is formed.

2. A process in accordance with claim 1 wherein said contact occurs in the presence of carbon monoxide.

3. A process in accordance with claim 1 wherein said contact occurs in the presence of hydrogen.

4. A process in accordance with claim 1 wherein said allylic ether is alkyl n-alkoxy-(n-2)-alkenoate where n is an integer equal to the number of carbon atoms in the main chain of the alkenoate group independent of any substitution thereon of one or more alkyl groups.

5. A process in accordance with claim 4 wherein said alkyl contains 1 to about 6 carbon atoms; said alkoxy contains 1 to about 6 carbon atoms and said alkenoate contains 3 to about 12 carbon atoms.

6. A process in accordance with claim 5 wherein said alkenoate contains 9 carbon atoms.

7. A process in accordance with claim 1 wherein said allylic ether is 1,1,n-trialkoxy-(n-2)-alkene where n is an integer equal to the number of carbon atoms in the alkene chain group independent of any substitution thereon of one or more alkyl groups.

8. A process in accordance with claim 7 wherein said alkoxy contains 1 to about 6 carbon atoms and said alkene contains 3 to about 12 carbon atoms.

9. A process in accordance with claim 8 wherein n is 9 and said alkene is nonene.

10. A process in accordance with claim 1 wherein said cobalt compound is a cobalt salt.

11. A process in accordance with claim 10 wherein said cobalt salt is a cobalt halide.

12. A process in accordance with claim 1 wherein said cobalt compound is a cobalt coordination compound.

13. A process in accordance with claim 12 wherein said cobalt coordination compound is a cobalt carbonyl complex.

14. A process in accordance with claim 13 wherein said cobalt carbonyl complex includes $Co_2(CO)_8$.

15. A process in accordance with claim 13 wherein said cobalt carbonyl complex includes a ligand selected from the group consisting of a phosphine, a phosphite, an aliphatic amine and a heterocyclic nitrogen-containing aromatic.

16. A process in accordance with claim 15 wherein said cobalt coordination compound is $Co_2(CO)_8$ and pyridine.

17. A process in accordance with claim 2 wherein said contact between said allylic ether and said alkanol occurs at a temperature in the range of between about 140° C. and about 250° C. and at a pressure in the range of between about 300 and about 4,000 psig.

18. A process in accordance with claim 17 wherein said reaction occurs under anhydrous conditions at a temperature in the range of between about 150° C. and about 180° C. and a pressure in the range of between about 500 and about 1000 psig.

19. A process in accordance with claim 2 wherein said allylic ether, said carbon monoxide, said alkanol and said cobalt compound are contacted with hydrogen gas.

20. A process for converting the ether group of an allylic ether to its corresponding acetal comprising contacting an allylic ether selected from the group consisting of methyl 9-methoxy-7-nonenoate and 1,1,9-trimethoxy-7-nonene with methanol and carbon monoxide in the presence of a catalytically effective amount of a cobalt compound at a temperature in the range of between about 140° C. and about 250° C. and a pressure in the range of between about 300 psig and about 4,000 psig whereby an acetal selected from the group consisting of methyl 9,9-dimethoxy-nonanoate and 1,1,9,9-tetramethoxynonane, respectively is formed.

21. A process in accordance with claim 20 wherein said reaction occurs under anhydrous conditions at a temperature in the range of between about 150° and about 180° C. and at a pressure in the range of between about 500 and about 1,000 psig.

22. A process in accordance with claim 20 wherein said cobalt compound is a cobalt coordination compound comprising $Co_2(CO)_8$.

23. A process in accordance with claim 20 wherein said cobalt carbonyl complex comprises $Co_2(CO)_8$ and pyridine.

24. A process in accordance with claim 20 wherein said cobalt compound is a cobalt halide.

25. A process in accordance with claim 24 wherein said cobalt halide is cobalt chloride.

* * * * *